United States Patent [19]

Passalacqua

[11] Patent Number: 4,605,553
[45] Date of Patent: Aug. 12, 1986

[54] DRY PRESSED POWDER STICK COMPOSITION AND VEHICLE THEREFOR

[76] Inventor: Peter Passalacqua, 185 Prospect Ave., Hackensack, N.J. 07601

[21] Appl. No.: 462,305

[22] Filed: Jan. 31, 1983

[51] Int. Cl.$^4$ .................. A61K 7/32; A61K 7/38; A61K 7/42; A61K 7/44
[52] U.S. Cl. .................................. 424/59; 424/60; 424/63; 424/66; 424/67; 424/68; 424/69
[58] Field of Search ................ 424/68, 69, 60, 59, 424/DIG. 5

[56] References Cited

U.S. PATENT DOCUMENTS

| | | | |
|---|---|---|---|
| 684,553 | 10/1901 | Rohde | 424/69 |
| 1,995,663 | 3/1935 | Bollmann | 424/69 |
| 2,218,586 | 10/1940 | Quaedvlieg | 424/69 |
| 2,373,933 | 4/1945 | Weeks | 424/69 |
| 2,389,770 | 11/1945 | Gaver | 424/69 |
| 2,626,257 | 1/1953 | Caldwell et al. | 424/69 |
| 2,749,277 | 6/1956 | Toulmin, Jr. | 424/69 X |
| 2,838,440 | 6/1958 | Thurmon | 424/69 |
| 2,864,743 | 12/1958 | Kattler et al. | 424/69 |
| 3,278,383 | 10/1966 | White et al. | 424/69 |

*Primary Examiner*—Dale R. Ore
*Attorney, Agent, or Firm*—W. Patrick Quast

[57] ABSTRACT

An improved dry pressed powder composition containing, by weight, about 1 to 10% a metal stearate, e.g. zinc stearate, about 1 to 10% alkaline metal carbonate, e.g. magnesium carbonate, about 10 to 50% of a naturally or synthetically derived cellulose or derivative thereof; and about 10 to 60% of aluminum potassium silicate; and a cosmetically effective amount of a cosmetically active ingredient, e.g. about 15 to 30% of aluminum chlorohydrate antiperspirant. The ingredients are blended together in a dry form and pressed into a stick-type form.

18 Claims, No Drawings

DRY PRESSED POWDER STICK COMPOSITION AND VEHICLE THEREFOR

BACKGROUND OF INVENTION

1. Field of the Invention

This invention relates to dry pressed powder compositions, and in particular, dry pressed powder compositions in a stick-type form containing, for example, an antiperspirant.

2. Prior Art

Current stick-type compositions, for example an antiperspirant, consist of a bacteriostat or other biologically active compound, for example an active antiperspirant such as zirconium or aluminum chlorohydrate, dispersed in a vehicle such as alcohol-based gels, e.g. ethanol, or a glycol such as propylene glycol. In these type of compositions, gelation is effected by the use of a soap, e.g. sodium stearate. The solid stick-type compositions may also contain other ingredients, such as water, humectants, gums, surfactants, dyes, perfumes, etc. These type compositions have drawbacks in that when applied to the skin, they have an undesirable wet feeling. Additionally, ethanol-based compositions are very volatile and will evaporate in the package at room temperature, volatility being further exaggerated at elevated temperatures. As a result of this volatility, the stick shrinks and becomes useless. Such a composition creates packaging problems and has a comparatively short shelf life. Glycol based compositions, on the other hand, do not have these disadvantages, but provide a product which is hard and waxy. As a result, this provides an undesirable feel when applied, has little covering capability and is sticky and wet feeling during and after application. Known vehicles for antiperspirants include volatile silicone in a wax-type base. This type formula has some of the same disadvantages as the previous compositions. Other cosmetic preparations, such as blushers and lipsticks, utilize fats and/or waxes such as beeswax, carnauba wax, candeli wax, microcrystalline wax, vegetable oils, castor oils, and the like. Vehicles of this type can only be used in certain formulations of cosmetic products because of the many technical and formulation problems. Compression of a powder into a stick form has been attempted for an antiperspirant but has not produced a successful product. Attempts to produce such products has resulted in hard sticks that are difficult to apply, e.g. difficult to deposit a sufficient amount of powder to be useful. Attempts have been made to reduce the degree of compression. However, when the degree of compression is reduced, the powder stick crumbles and does not stay in a compressed form. Other attempts to solve these problems have included applying a separate wrapper of a dry film or film form of coating to the stick composition to prevent crumbling or shedding or dusting of the loosely compacted powder, see for example U.S. Pat. No. 3,471,611 to Scott et al. Other attempts include the use of gums or other material that has adhesive binders, see for example U.S. Pat. No. 3,800,034 to Kircher. None of these attempts to produce an improved dry pressed powder composition have been successful.

More specifically, the following U.S. patents are relevant to applicant's invention: U.S. Pat. Nos. 1,968,475 to Beckwith et al; 3,471,611 to Scott et al; 3,800,034 to Kircher; 4,126,679 to Davy et al; 4,226,889 to Yuhas; 4,322,400 to Yuhas; and German Pat. No. 2,852,988.

Kircher et al describes a dry pressed powder stick for makeup composition. The majority of the composition of this pressed powder stick is finely divided chalk, i.e., calcium carbonate. This stick can include such ingredients as magnesium carbonate, zinc oxide, starch and starch derivatives with the use of certain forms of cellulose, such as methyl and ethyl cellulose, as binders. The material, including binders, can be formed into sticks by extrusion and drying of the liquid or by pressing or molding operations. Pressures used in forming the dry pressed product are not indicated. The German Patent shows a powder stick formed by pressure of three and one half to five and one half kilograms per square centimeter. Methyl cellulose is listed as one of the binder materials which can be used. Other contents listed include: magnesium carbonate, zinc oxide and silicon dioxide.

Scott et al shows a compressed powder cosmetic article which uses a fragile film formed of materials which include cellulose of the methyl, ethyl or nitro forms. The film forming materials are deposited on the cosmetic powder after compression into its commercial form.

Beckwith et al shows a powder cosmetic composition which can be formed in a mold, such as a previously used compact container by means of the evaporation of a solvent in air. The powder base may include magnesium carbonate or zinc oxide among other materials.

Davy et al shows the formation of a cosmetic stick such as a deodorant or antiperspirant stick by means of the addition of powdered materials usually astringent salts to a matrix of silicon oil and alcohol. The sticks are formed by pouring the mixture at elevated temperatures into molds and cooling the material.

The Yuhas patents show solid stick-type cosmetic compositions formed from stearates, water, and an "active" material.

OBJECTS AND SUMMARY OF THE INVENTION

It is an object of this invention to provide an improved cosmetic stick composition.

A further object of this invention is to provide a new vehicle capable of use in cosmetic stick compositions having a variety of uses.

Still another object of this invention is to provide a vehicle suitable for use in deodorant sticks, lipsticks, talc sticks and other cosmetic stick applications.

It is a further object of this invention to provide a unique form of antiperspirant composition, which eliminates most of the disadvantages of the previously known compositions.

These and other objects of this invention, which will be apparent from the ensuing specification and claims are achieved by a composition of a dry pressed powder containing, by weight, about 1% to 10% of a metal stearate, e.g. zinc stearate, about 1 to 10% alkaline metal carbonate, e.g. magnesium carbonate, about 10 to 50% of a naturally or synthetically derived cellulose or derivative thereof, and about 10% to 60% of aluminum potassium sillicate; and a cosmetically effective amount of an active cosmetic ingredient, e.g. an antiperspirant such as aluminum chlorohydrate. The ingredients are blended together in a dry form and pressed into a stick-type form.

DETAILED DESCRIPTION OF THE INVENTION

This invention is directed to a dry pressed powder composition that can be made with virtually no liquid additives or liquids that make up less than 10% of the product. The composition includes, by weight, about 1% to 10% of a metal stearate. The metal may be zinc, aluminium or an alkaline metal. By the term "alkaline metal" as used herein, it is meant alkaline earth metal and alkali metal compounds such as magnesium, calcium, sodium, potassium, lithium and zinc. The preferred metal stearate is zinc stearate.

Additionally, the powdered composition includes about 1 to 10% alkaline metal carbonate, preferably about 2 to 5%.

It has been found that the alkaline metal carbonate and metal stearate should be added at from about 1% to 10% each. Any level below this will cause poor compressibility of the stick. Higher levels will cause poor cosmetic feel when used. The carbonate improves the strength of the stick while the stearate acts as a lubricant to aid in extrusion or otherwise forming the composition into a stick form, as well as improving the adherance and application of the composition to the skin. The use of a lubricant is important when the mixture is extruded into stick form, for the dry materials, particularly the carbonate, are highly abrasive and the incorporation of a lubricant facilitates the extrusion operation.

The composition additionally includes from about 10 to 50%, and preferably from about 28 to 50%, of a naturally or synthetically derived cellulose or derivative thereof. The size of the celluose particles is preferably microcrystalline. Cellulose derivatives which could be used include carboxy methyl cellulose, sodium carboxymethyl cellulose, methyl and ethyl cellulose, gum acacia, and alpha cellulose.

The cellulose enhances flowability of the powder blend under formation pressures and adds to the cosmetic feel on the skin. Additionally, it functions as a binder to assist in binding the powdered material together and provides the necessary strength for the stick.

The composition further contains from about 10 to 60%, and preferably from about 29 to 40% of aluminum potassium silicate.

The aluminum potassium silicate composition is a powder that adds to the compressibility of the stick and acts as a binder to hold the powder composition in a solid-stick form. The use of the aluminum potassium silicate enables the formulation to have solid-stick properties, while still maintaining cosmetic feel and performing its useful function as, for example, an antiperspirant composition. The aluminum potassium silicate used is of a form that the particles of aluminum potassium silicate act as a cohesive force on the other ingredients in the powdered composition, as well as add to the cosmetic properties of the composition.

The fifth essential ingredient of the cosmetic stick composition of this invention is an "active ingredient", by which is meant an ingredient which it is desired to deposit on the skin of a human being. Such active ingredients can include bacteriostats and fungistats, pigments and dyes or other colorants, perfumes, emollients, ultraviolet absorbers or "sun screens", corn starch, and talc. Of course, any active ingredient must be stable in the environment provided by the other ingredients. Particularly stable active ingredients are antiperspirant materials, such as aluminum chlorohydrate or aluminum zirconium chlorohydrate complex. Depending upon the intended end use of the cosmetic stick composition, the cosmetically effective amount of the "active ingredient" can vary from as little as 0.05 weight percent or less up to 50 weight percent or more of the total weight of the composition and preferably about 10 to 30%.

When the active ingredient is an antiperspirant, such as aluminum chlorohydrate or aluminum zirconium chlorohydrate complex, the ingredient is present in the composition at from about 10 to 40% by weight of composition, and preferably 15% to 30%.

Perfume sticks can be prepared by including one or more aromatic substances into the composition. These aromatic substances may include natural products such as essential oils, flower oils, natural extracts from resins, gums, balsams, beans, mosses and other plants, and animal fixtures such as ambergris and musk, as well as synthetic aromatic materials. The variety of such materials is too great to list.

Another type of stick-type cosmetic product which may be prepared in accordance with this invention is a sun stick, in which the active ingredient is an ultraviolet absorber such as p-aminobenzoic acid, its salts or its esters, as well as N-substituted derivatives such as p(dimethylamino) benzoic acid, an anthranilate, a salicylate, esters of cinnamic acid, dihydroxycinnamic acid or trihydroxycinnamic acid, diphenyl-butadiene, stilbene, a naptholsulfonate, a coumarin derivative, a quinine salt, a quinoline derivative, hydroquinone, tannic acid, zinc oxide, dioxybenzone and oxybenzone.

Still another cosmetic stick composition within the scope of this invention is an emollient and lubricating composition wherein the "active ingredient" is a compatible humectant or emollient composition. Such a composition includes sugar derivatives, for example sucrose and glucose which have been esterified with long chain fatty acids such as stearic acid, e.g. sucrose monstearate and/or sucrose distearate, and glucose derivatives such as methyl glucoside sesquistearate and propoxylated glucose.

The compositions of this invention may also be make-up sticks, in which a solid pigment is to be applied, such as a rouge, lipstick, eye-shadow, eye-liner, etc., and is incorporated into the composition as the active ingredient. The pigments include titanium dioxide, zinc oxide, iron oxide and the like, aluminum lake, barium lake, calcium lake, strontium lake, tetrabromofluorescein, tetrabromotetrachlorofluorescein, dibromoflourescein and the like.

A further cosmetic formulation embodying the present invention comprises a solid talc stick, in which the "active ingredient" is powdered cosmetic grade talc or corn starch, which typically has particles whose sizes are about 200 to about 400 mesh (U.S. Standard Series). It is also within the scope of this invention that two or more active substances can be present. For example, a talc stick can also include a bacteriostat and/or fungistat for use as a medicated powder stick, for example a foot powder stick, or it can contain a pigment for use as a pigmented talc stick.

Apart from the aforementioned ingredients, the cosmetic stick composition of this invention may contain small amounts of ingredients intended primarily to modify the properties of the stick compositions, and not for deposit on human skin, for example, odorants and colorants, which are primarily intended to impart a color or fragance to the stick composition. By the term "odorant", as employed herein, is meant an additive such as a perfume which give the composition a desired odor, as well as an odor mask, which is intended to mask the characteristic odors of othe ingredients and thus provide an "unscented" product. By the term "colorant", as employed herein, is meant a dye or other agent employed herein to impart a particular color to or to mask a particular color of the deodorant stick composition.

For all of the foregoing compositions, it is well within the skill of the artisan, with the assistance provided by the teachings of this specification to formulate useful dry pressed powder compositions having different cosmetically active ingredients.

Generally, all of the aforementioned ingredients, most of which are powdered ingredients are dry blended to form a homogeneous mixture. The blended powders are then filled into a punch and dye press mold. An hydraulic press or an equivalent machine is used to stamp out the finished stick-type form. Pressures of from about 100 psi to 3,000 psi may be used, with a preferred range of 300 about to 1,200 psi. This may be accomplished at from 20° C. to 80° C. The stick can subsequently be placed into the finished container.

The following are non-limiting Examples of powdered antiperspirant compositions of this invention which have been formed into sticks:

| Ingredients (by weight) % | Example 1 | Example 2 | Example 3 | Example 4 |
|---|---|---|---|---|
| Aluminum Chlorohydrate | 15.0 | 20.0 | 30.0 | — |
| Zinc Stearate | 1.0 | 10.0 | 5.0 | 5.0 |
| Magnesium Carbonate | 5.0 | 2.0 | 5.0 | 2.0 |
| Alpha Cellulose | 50.0 | 28.0 | 30.0 | 33.0 |
| Aluminum Potassium Silicate Composition | 29.0 | 40.0 | 30.0 | 40.0 |
| Aluminum Zirconium Chlorohydrate Complex | — | — | — | 20.0 |

These sticks are easily formed, have excellent feel and efficacy, and do not crumble or deteriorate.

What is claimed is:

1. In an improved dry pressed powder stick composition consisting essentially of, by weight:
   (a) about 1 to 10% of a metal stearate;
   (b) about 1 to 10% of an alkaline metal carbonate;
   (c) about 10% to 50% of a naturally or synthetically derived cellulose or derivative thereof;
   (d) about 0.05% up to 50% of cosmetically active ingredient which is stable in the composition, wherein the improvement comprises about 10% to 60% of aluminum potassium silicate,
   said dry pressed powder stick composition formed by mixing all of the above ingredients in a dry blend to form a homogeneous mixture, loading the mixture into a mold, and then applying pressures from about 100 psi to 3000 psi to the mixture in the mold at a temperature from 20° C. to 80° C. for a time sufficient to achieve the pressed stick composition.

2. In an improved dry pressed powder stick composition consisting essentially of, by weight:
   (a) about 1 to 10% of metal stearate;
   (b) about 2 to 5% of an alkaline metal carbonate;
   (c) about 28 to 50% of a naturally or synthetically derived cellulose or derivative thereof;
   (d) about 0.05% up to 50% of cosmetically active ingredient which is stable in the composition, wherein the improvement comprises about 29% to 40% of aluminum potassium silicate,
   said dry pressed powder stick composition formed by mixing all of the above ingredients in a dry blend to form a homogeneous mixture loading the mixture into a mold, and then applying pressures from about 100 psi to 3000 psi to the mixture in the mold at a temperature from 20° C. to 80° C. for a time sufficient to achieve the pressed stick composition.

3. The composition of claim 1 or 2, wherein the metal stearate is zinc stearate.

4. The composition of claim 1 or 2, wherein the alkaline metal carbonate is magnesium carbonate.

5. The composition of claim 1 or 2, wherein the active ingredient is aluminum chlorohydrate.

6. The composition of claim 1 or 2, wherein the active ingredient is aluminum zirconium chlorohydrate complex.

7. The composition of claim 1 or 2, wherein the cellulose is alpha cellulose.

8. The composition of claim 1 or 2, wherein the metal stearate is zinc stearate, the alkaline metal carbonate is magnesium carbonate, the active ingredient is aluminum chlorohydrate, and the cellulose is alpha cellulose.

9. The composition of claim 1 or 2, wherein the active ingredient is an antiperspirant.

10. The composition of claim 1 or 2, wherein the active ingredient is a fungistat.

11. The composition of claim 1 or 2, wherein the active ingredient is a bacteriostat.

12. The composition of claim 1 or 2, wherein the active ingredient is a colorant.

13. The composition of claim 1 or 2, wherein the active ingredient is a perfume.

14. The composition of claim 1 or 2, wherein the active ingredient is an emollient.

15. The composition of claim 1 or 2, wherein the active ingredient is an ultraviolet absorber.

16. The composition of claim 1 or 2, wherein the active ingredient is talc.

17. The composition of claim 1 or 2, wherein the active ingredient is corn starch.

18. The composition claimed in either claim 1 or 2 wherein the pressures applied are between 300 to 1200 psi.

* * * * *